(12) United States Patent
Park

(10) Patent No.: US 10,203,332 B2
(45) Date of Patent: Feb. 12, 2019

(54) APPARATUS FOR AND METHOD OF SEPARATING TARGET MATTER

(71) Applicant: Samsung Electronics Co., Ltd., Suwon-si (KR)

(72) Inventor: Jongmyeon Park, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/505,827

(22) PCT Filed: Aug. 4, 2015

(86) PCT No.: PCT/KR2015/008099
§ 371 (c)(1),
(2) Date: Feb. 22, 2017

(87) PCT Pub. No.: WO2016/028011
PCT Pub. Date: Feb. 25, 2016

(65) Prior Publication Data
US 2017/0276682 A1  Sep. 28, 2017

(30) Foreign Application Priority Data

Aug. 22, 2014  (KR) .................... 10-2014-0109966

(51) Int. Cl.
*B03C 1/01* (2006.01)
*G01N 33/574* (2006.01)
(Continued)

(52) U.S. Cl.
CPC ......... *G01N 33/57492* (2013.01); *B03C 1/01* (2013.01); *B03C 1/288* (2013.01);
(Continued)

(58) Field of Classification Search
CPC .. B03C 1/005; B03C 1/01; B03C 1/28; B03C 1/288; B03C 1/32; B03C 2201/18;
(Continued)

(56) References Cited

U.S. PATENT DOCUMENTS 4,272,510 A * 6/1981 Smith .................... B03C 1/0332
427/127
5,397,539 A * 3/1995 Hayashi ........... G01N 35/00594
422/552

(Continued)

FOREIGN PATENT DOCUMENTS

JP  2011-506935 A  3/2011
KR  10-2012-0060140 A  6/2012
(Continued)

OTHER PUBLICATIONS

International Search Report issued in counterpart International Application No. PCT/KR2015/008099 dated Nov. 23, 2015 (2 pages).

*Primary Examiner* — Joseph C Rodriguez
(74) *Attorney, Agent, or Firm* — NSIP Law

(57) ABSTRACT

An apparatus and method for separating a target material. The apparatus for separating a target matter includes a mixture including a target matter, a density gradient material layer disposed under the mixture and having a greater density than a density of the mixture, magnetic beads including a magnetic material and binding to the target matter to form a complex, and a magnetic field generating device applying a magnetic field to the complex to precipitate the complex at the bottom of the density gradient material layer.

14 Claims, 8 Drawing Sheets

(51) Int. Cl.
  *G01N 33/53* (2006.01)
  *B03C 1/28* (2006.01)
  *C12M 1/00* (2006.01)
  *G01N 33/537* (2006.01)
  *G01N 33/543* (2006.01)

(52) U.S. Cl.
  CPC .............. *C12M 47/04* (2013.01); *G01N 33/53* (2013.01); *G01N 33/5375* (2013.01); *G01N 33/54326* (2013.01); *B03C 2201/18* (2013.01); *B03C 2201/26* (2013.01)

(58) Field of Classification Search
  CPC .......... B03C 2201/26; G01N 33/54326; G01N 33/54333; G01N 33/57492; G01N 35/0098
  See application file for complete search history.

(56) References Cited

U.S. PATENT DOCUMENTS

| | | | | |
|---|---|---|---|---|
| 5,780,224 | A * | 7/1998 | Collins | C12Q 1/6813 435/5 |
| 6,143,578 | A * | 11/2000 | Bendele | B03C 1/0332 209/214 |
| 6,368,561 | B1 * | 4/2002 | Rutishauser | G01N 35/0098 210/205 |
| 6,447,729 | B1 * | 9/2002 | Tuunanen | B01L 3/02 422/527 |
| 6,672,458 | B2 * | 1/2004 | Hansen | B01L 7/52 209/224 |
| 6,890,742 | B2 * | 5/2005 | Ammann | B01F 9/0001 435/6.11 |
| 7,998,696 | B2 | 8/2011 | Zaugg et al. | |
| 8,551,333 | B2 * | 10/2013 | Lin | B01L 3/502761 210/222 |
| 8,986,945 | B2 * | 3/2015 | Lin | G01N 33/5094 435/261 |
| 9,259,732 | B2 * | 2/2016 | Davis | B03C 1/0332 |
| 9,618,139 | B2 * | 4/2017 | Handique | B01L 7/52 |
| 9,636,647 | B2 * | 5/2017 | Vincent | B01F 11/0002 |
| 2006/0254972 | A1 | 11/2006 | Tai et al. | |
| 2007/0059782 | A1 | 3/2007 | Graham et al. | |
| 2007/0196820 | A1 | 8/2007 | Kapur et al. | |
| 2008/0206757 | A1 | 8/2008 | Lin et al. | |
| 2009/0028759 | A1 * | 1/2009 | Su | G01N 35/0098 422/400 |
| 2009/0220979 | A1 | 9/2009 | Davis et al. | |
| 2010/0009383 | A1 | 1/2010 | Kiesewetter et al. | |
| 2012/0142089 | A1 | 6/2012 | Park | |
| 2012/0252088 | A1 | 10/2012 | Zhang et al. | |
| 2013/0026079 | A1 * | 1/2013 | Davis | B03C 1/0332 209/215 |
| 2013/0043191 | A1 * | 2/2013 | Park | C12M 33/06 210/695 |
| 2013/0273552 | A1 * | 10/2013 | Ohashi | B01L 3/5025 435/6.12 |
| 2014/0302483 | A1 * | 10/2014 | Kauling | B01D 21/00 435/2 |
| 2015/0056649 | A1 | 2/2015 | Araki et al. | |

FOREIGN PATENT DOCUMENTS

| | | |
|---|---|---|
| KR | 10-2014-0078189 A | 6/2014 |
| WO | WO 2013/105612 A1 | 7/2013 |
| WO | WO 2013/166170 A1 | 11/2013 |

* cited by examiner

APPARATUS FOR AND METHOD OF SEPARATING TARGET MATTER

CROSS-REFERENCE TO RELATED APPLICATIONS

This application claims the benefit under 35 USC 119(a) of PCT Application No. PCT/KR2015/008099, filed on Aug. 4, 2015, which claims the benefit of Korean Patent Application No. 10-2014-0109966 filed Aug. 22, 2014, in the Korean Intellectual Property Office, the entire disclosure of which is incorporated herein by reference for all purposes.

TECHNICAL FIELD

The present disclosure relates to apparatuses for and methods of separating a target matter, and more particularly, to apparatuses for and methods of separating a target matter from a mixture.

BACKGROUND ART

In recent years, techniques of separating a target material from a mixture and analyzing the target material have been used in a wide variety of applications. Particularly, these techniques have been used for medical research on separation of viruses and cancer cells. In treating cancer patients, circulating tumor cells (CTCs) are detected in the blood of patients and observed in order to determine the survival probability, diagnose cancer recurrence, and measure the effects of cancer treatment.

CTCs are regarded as the major factor contributing to death in cancer patients. Most cancer patients die of metastasis of cancer cells from primary tissues or organs to other tissues or organs not directly connected therebetween. Thus, early detection and monitoring of metastasis is a critical factor for the survival of cancer patients. In addition, CTCs may be used for detecting metastasis. In general, cancers metastasize through blood, and thus, CTCs may be used as a marker to diagnose the metastasis of cancer cells. However, although CTCs exist in blood, it is very difficult to accurately identify their existence. Even though CTCs are identified in blood, the amount for analyzing the characteristics of the detected CTCs is limited because selectively separating CTCs from erythrocytes and leukocytes contained in blood is limited.

One of the related arts for separating CTCs discloses a method of separating blood into erythrocytes, leukocytes, CTCs, and serum via a density gradient condition to manually isolate a desired layer. However, according to this method, leukocytes and CTCs are not separated from each other but exist in a mixture, and thus, the separation efficiency of CTCs from leukocytes is small.

Other related arts disclose cell margination and multi-orifice separation based on fluid dynamics principles. The former is a technology whereby the number of small cells such as erythrocytes is relatively reduced and the number of other cells is increased by using a phenomenon which occurs in actual blood vessels in which small particles gather in the inner part of the blood vessels and large particles move outside. The latter is a principle whereby a channel along which a fluid flows has an expanded tube section to respectively gather large particles and small particles outside and in the middle of the channel according to the Reynolds number. However, it is difficult to selectively separate a desired target cell from blood by using this principle, and there is limitation in treating a volume of several ml because the fluid flow rate is slow. Also, it is necessary to dilute a fluid by several hundred times in order to control the Reynolds number, and thus, there is a limitation in that samples of several hundred ml should be actually treated. Accordingly, there still remains a need for a method of efficiently separating a target matter such as CTCs from a mixture such as blood.

DETAILED DESCRIPTION OF THE INVENTION

Technical Solution

Provided are apparatuses for and method of separating a target matter from a mixture.

Advantageous Effects

Hereinafter, the target matter separating apparatus 100 and the target matter separating method 1000 according to an exemplary embodiment are described above with reference to FIGS. 1 to 10. According to the target matter separating apparatus 100 and the target matter separating method 1000, the target matters 126 may be efficiently separated with high extraction rate and high purity.

BEST MODE

Figure 1:
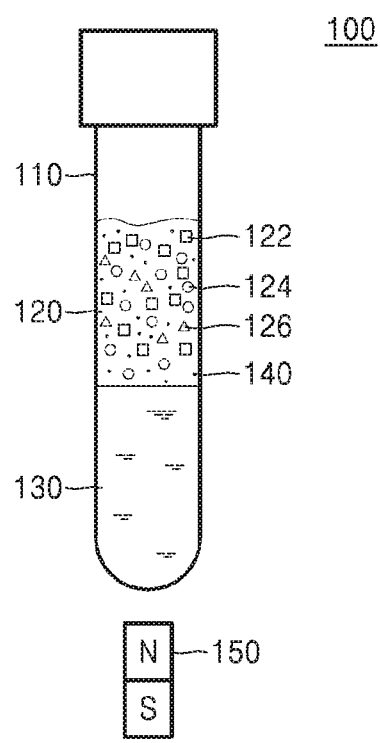
FIG. 1 is a diagram illustrating an apparatus for separating a target matter according to an exemplary embodiment.

According to an aspect of an exemplary embodiment, an apparatus for separating a target matter includes: a mixture including a target matter; a density gradient material layer disposed under the mixture and having a greater density than a density of the mixture; magnetic beads including a magnetic material and binding to the target matter to form a complex; and a magnetic field generating device applying a magnetic field to the complex to precipitate the complex at the bottom of the density gradient material layer.

The mixture may include at least one selected from the group consisting of blood, bone marrow, saliva, tear, urine, semen, or mucous fluid. The target matter may include circulating tumor cells (CTCs). The mixture may be blood, and a density of the density gradient material layer may be greater than a density of a leukocyte contained in the blood. A density of the magnetic bead may be greater than a density of the density gradient material layer.

A density of the density gradient material layer may be in a range of about 1.077 g/mL to about 1.2 g/mL. The magnetic bead may include a paramagnetic bead. The magnetic bead may include a ligand specifically binding to a surface marker contained in the target matter. The target matter may include CTCs, the surface marker may include at least one selected from the group consisting of EpCAM, c-Met, cytokeratines, CD45, Her2, Caveolin, EGFR, and IGFR existing on the surfaces of the CTCs, and the ligand may include an antibody capable of binding to the surface marker.

The apparatus may further include a first chamber configured to accommodate the mixture and the density gradient material layer, wherein an opening is formed at a lower portion of the density gradient material layer.

The apparatus may further include a second chamber in communication with the first chamber through the opening.

The apparatus may further include a valve configured to control opening and closing of the opening.

A lower surface of the first chamber may be downwardly slanted toward the second chamber.

The magnetic field generating device may introduce the complex precipitated at the bottom of the first chamber into the second chamber.

According to an aspect of another exemplary embodiment, a method of selectively separating a target matter contained in a mixture includes: forming a complex by binding magnetic beads including a magnetic material to the target matter; introducing a density gradient material layer having a greater density than a density of the mixture into the first chamber; introducing the mixture into the first chamber; and precipitating the complex at the bottom of the density gradient material layer by applying a magnetic field to the complex.

A density of the magnetic bead may be greater than a density of the density gradient material layer.

The magnetic bead may include a ligand capable of specifically binding to a surface marker contained in the target matter.

The target matter may include CTCs, the surface marker may include at least one selected from the group consisting of EpCAM, c-Met, cytokeratines, CD45, Her2, Caveolin, EGFR, and IGFR existing on the surface of the CTCs, and the ligand may include an antibody capable of binding to the surface marker.

The method may further include moving the complex precipitated at the bottom of the density gradient material layer into the second chamber in communication with the first chamber by applying a magnetic field to the complex.

MODE OF THE INVENTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

FIG. 1 is a diagram illustrating an apparatus 100 for separating a target matter according to an exemplary embodiment. Referring to FIG. 1, the target matter separating apparatus 100 includes a mixture 120 including target matters 126, a density gradient material layer 130 disposed under the mixture 120 and having a greater density than a density of the mixture 120, magnetic beads 140 including a magnetic material and binding to the target matters 126 to form complexes, and a magnetic field generating device 150 applying a magnetic field to the complexes to precipitate the complexes at the bottom of the density gradient material layer 130.

The target matter separating apparatus 100 illustrated in FIG. 1 may be an apparatus for selectively separating the target matters 126 from the mixture 120. The mixture 120 may be a gas, liquid, or viscous fluid in which various materials are mixed. However, the mixture 120 is no limited thereto. When the mixture 120 is a biological sample, the mixture 120 may be blood, bone marrow, saliva, tear, urine, semen, or mucous fluid of a living organism or any combination thereof. In addition, the mixture 120 may further include a biopsy sample, a tissue sample, a cell suspension prepared by suspending separated cells in a liquid medium, and cell cultures. In addition, the mixture 120 may include the target matters 126 to be selectively separated and observed.

When the mixture 120 is a biological sample, the target matters 120 may be cancer cells or tumor cells selected from the group consisting of cells of bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal cancer, ovarian cancer, pancreatic cancer, gallbladder cancer, prostate cancer, thyroid carcinoma, osteosarcoma, rhabdomyosarcoma, synovial sarcoma, kaposi sarcoma, leiomyosarcoma, malignant gibrous histiocytoma, fibrosarcoma, adult T-cell leukemia, lymphoma, multiple myeloma, glioblastoma/astrocytoma, melanoma, mesothelioma, and tumors Will Chelmsford. However, these are exemplarily described, without being limited thereto.

FIG. 1 exemplarily illustrates that the mixture 120 is blood. As illustrated in FIG. 1, the mixture 120 may include erythrocytes 122, leukocytes 124, and CTCs which are the target matters 126. The CTCs 126 may be separated from the mixture 120 as described above and may be used for diagnosis of metastasis of cancer patients and research on cancer cells. The target matters 126 contained in mixture 120 may be bound to the magnetic beads 140 before the mixture 120 is introduced into a first chamber 110. Alternatively, the magnetic beads 140 may be added to the mixture 120 after the mixture 120 is introduced in the first chamber 110. That is, in the first chamber 110, the target matters 126 may bind to the magnetic beads 140, thereby forming the complexes 145.

The density gradient material layer 130 may be formed of a material having a greater density than that of the mixture 120. In this regard, any material having a greater density than the mixture 120 may be used to form the density gradient material layer 130, and the density of the density gradient material layer 130 may be constantly maintained or gradually changed, without being limited thereto. A Ficoll product manufactured by Pharmacia Corporation may be used to form the density gradient material layer 130. Ficoll is a compound prepared by polymerization of sugar and epichlorohydrin and has a density of about 1.077 g/mL. A Percoll product manufactured by Pharmacia Corporation may also be used to form the density gradient material layer 130. Percoll is a colloidal silica having a polyvinylpyrrolidone coating layer and has a density of about 1.1 to about 1.2 g/mL. The afore-mentioned Ficoll and Percoll products have greater densities than leukocytes having a density of 1.07 g/mL). Thus, leukocytes may not be precipitated at the bottom of the density gradient material layer 130 in a process of precipitating CTCs that are the target matters, which will be described later.

The density gradient material layer 130 and the mixture 120 are introduced into the first chamber 110. A structure of the first chamber 110 will be described later in detail. First, the density gradient material layer 130 may be introduced into the first chamber 110, and then the mixture 120 may be introduced into the first chamber 110 to be above the density gradient material layer 130. Since the density of the density gradient material layer 130 is greater than that of the mixture 120, the mixture 120 may be maintained on the density gradient material layer 130.

Figure 2:
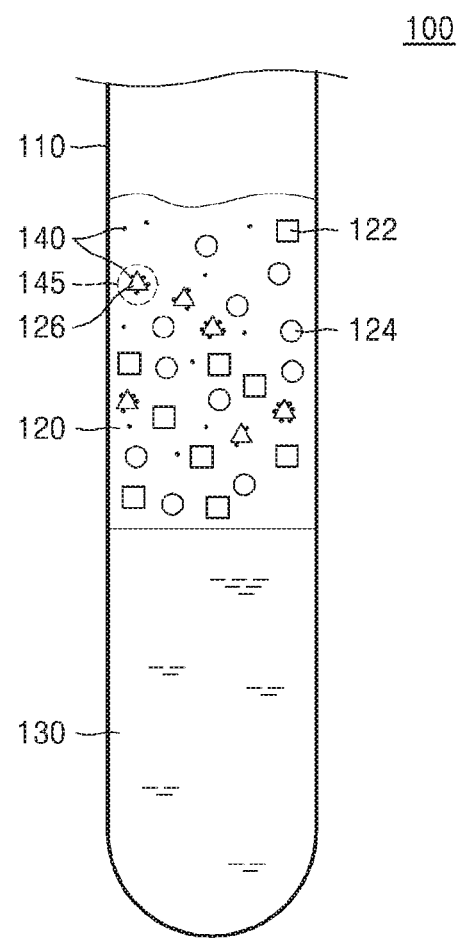
FIG. 2 is a diagram illustrating an example of binding of magnetic beads to target matters in a mixture illustrated in FIG. 1.

FIG. 2 is a diagram illustrating an example of binding of the magnetic beads 140 to the target matters 126 in the mixture 120 illustrated in FIG. 1. Referring to FIG. 2, the magnetic beads 140 may bind to the target matters 126 to form the complexes 145. The complexes 145 may be formed before or after the mixture 120 is introduced into the first chamber 110 as described above. The magnetic beads 140 may bind to the target matters 126 while being introduced and mixed into the mixture 120, and the numbers of magnetic beads 140 included in the complexes 145 may vary. The magnetic beads 140 may include a magnetic material. The magnetic material refers to a material magnetized in accordance with an intensity of a magnetic field commonly generated in laboratories. The magnetic material may include paramagnetic materials such as aluminum, tin, platinum, and iridium. However, these materials are exemplarily described, any material affected by an external magnetic field may be included the magnetic beads 140 as the magnetic material. In addition, a material such as polystyrene may be coated on surfaces of the magnetic beads 140.

The magnetic beads 140 may have various densities. According to an exemplarily embodiment, the magnetic beads 140 may have a greater density than that of leukocytes for an efficiently separation of the target matters 126 from the leukocytes. Particularly, the magnetic beads 140 may have a density of about 1.3 g/cm$^3$ to about 2.0 g/cm$^3$, without being limited thereto.

The magnetic beads 140 may include ligands specifically binding to surface markers contained in the target matters 126. The surface marker may be protein, sugar, lipid, or nucleic acid existing on the surfaces of the target matters 126 or any combination thereof. The surface marker may vary according to types of the target matters 126. When the target matters 126 are CTCs as illustrated in FIG. 1, the surface marker may be protein specifically expressed in tumor cells and exhibited on a cell membrane, i.e., antigen. Particularly, the surface marker may include at least one selected from the group consisting of EpCAM, c-Met, cytokeratines, CD45, and Her2.

The ligands of the magnetic beads 140 may bind to the surface markers. As described above, when the surface marker includes at least one selected from the group consisting of EpCAM, c-Met, cytokeratines, CD45, and Her2, the ligand may be an antibody capable of specifically binding to these proteins. The antibody specifically binds only to the surface marker to allow the magnetic beads 140 to selectively bind only to the target matters 126.

The ligand may exist in a bounding state with respect to the surface of the magnetic beads 140. For example, when the ligand is an antibody, a constant region of the antibody may bind to the surfaces of the magnetic beads 140 such that an antigen-binding site is exposed. The magnetic beads 140 may be coated on the surface thereof with a compound having an electric charge to facilitate the binding of the ligand to the surface marker. The compound having the electric charge on the surface thereof may be a compound having a functional group selected from the group consisting of a carboxyl group, a sulfonic acid group, a phosphoric acid group, an amine group, an imine group, and any combination thereof, without being limited thereto.

Since the magnetic beads 140 include the ligands on the surfaces thereof and the ligands specifically bind to the surface markers of the target matters 126 as described above, the magnetic beads 140 may bind to only to the target matters 126 to be separated. In addition, when the magnetic beads 140 bind to the target matters 126, the complexes 145 may be formed.

Figure 3:
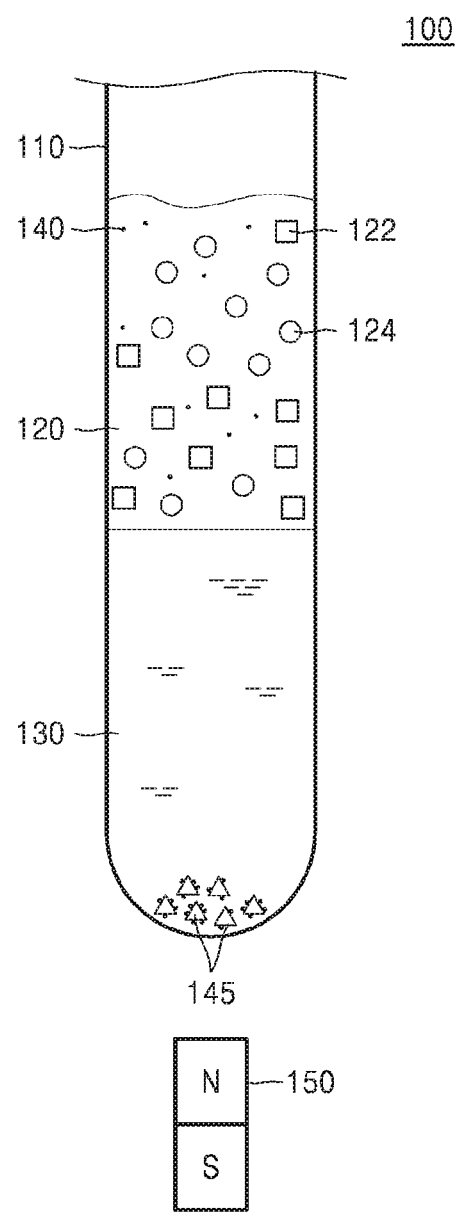
FIG. 3 is a diagram illustrating complexes depositing at the bottom of a density gradient material layer by using a magnetic field generating device.

FIG. 3 is a diagram illustrating the complexes 145 depositing at the bottom of the density gradient material layer 130 due to a magnetic field generated by the magnetic field generating device 150.

Referring to FIG. 3, the complexes 145 may be deposited at the bottom of the density gradient material layer 130 according to a magnetic field generated by the magnetic field generating device 150 disposed below the first chamber 110. The magnetic field generating device 150 may be a permanent magnet, a semi-permanent magnet, a current coil, or the like, without being limited thereto. The magnetic field generating device 150 may be disposed to be spaced apart from the first chamber 110 as illustrated in FIG. 3. However, the magnetic field generating device 150 may also be mounted on the bottom surface of the first chamber 110. A downward force is applied to the complex 145 including the magnetic beads 140 toward the bottom of the density gradient material layer 130 by the magnetic field generated by the magnetic field generating device 150. On the contrary, since the magnetic beads 140 do not bind to the erythrocytes 122 or the leukocytes 124, the erythrocytes 122 or the leukocytes 124 are not affected by the magnetic field. Thus, only the complexes 145 may be selectively deposited at the bottom of the density gradient material layer 130 due to a magnetic force. As a result, the target matters 126 may be separated from the mixture 120.

Figure 4:
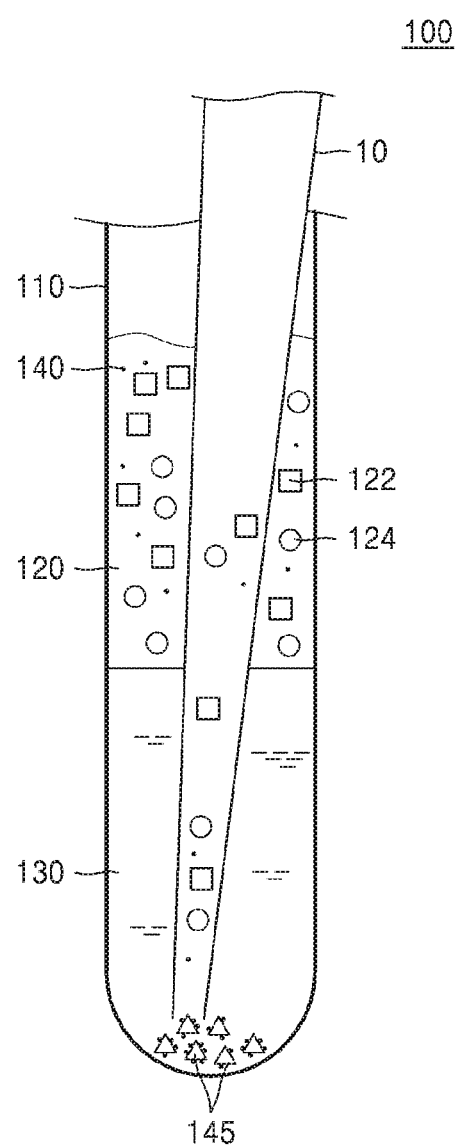
FIG. 4 is a diagram illustrating a general extraction process by using a pipette.

When the complexes 145 are deposited at the bottom of the density gradient material layer 130 as illustrated in FIG. 3, the deposited complexes 145 need to be extracted. FIG. 4 is a diagram illustrating a general extraction process by using a pipette 10.

Referring to FIG. 4, when the complexes 145 are extracted using the pipette 10, the complexes 145 pass through a layer of the mixture 120. While the pipette 10 passes through the mixture layer, other materials such as the erythrocytes 122 or the leukocytes 124 existing in the mixture 120 may be introduced into the pipette 10. In addition, the mixture 120 introduced into the pipette 10 may have an adverse influence on the purity of the target matters 126 to be separated. Thus, there is a need to use another method of recovering the target matters 126 without using the pipette 10.

Figure 5:
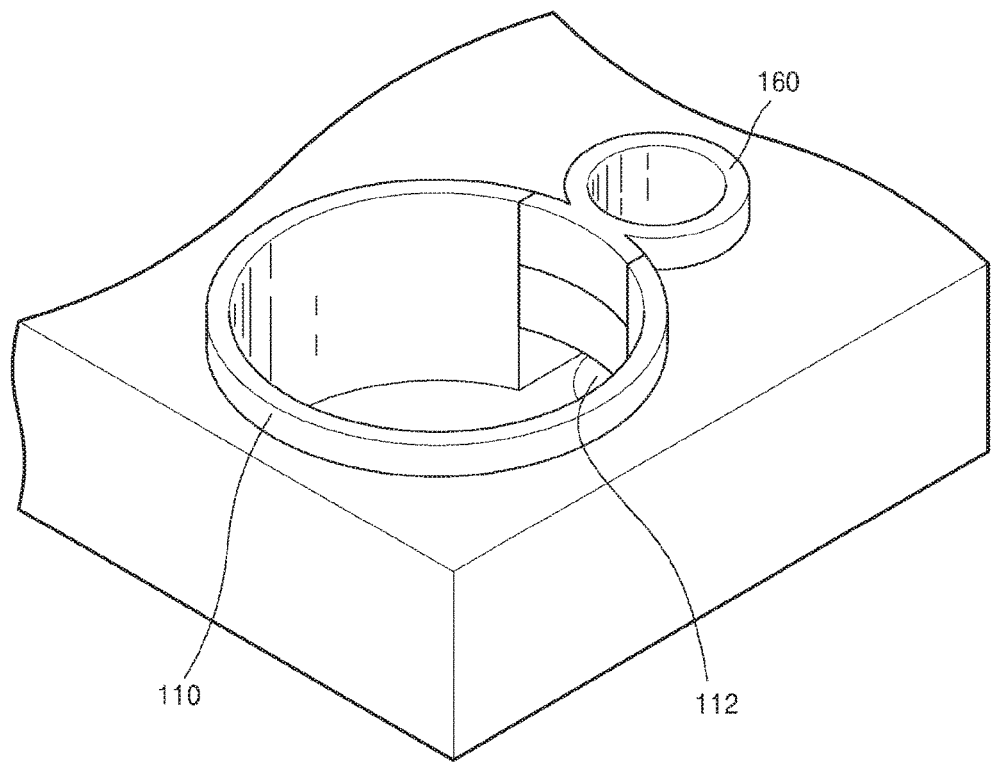
FIG. 5 is a diagram illustrating a first chamber and a second chamber used to recover a target matter.

FIG. 5 is a diagram illustrating the first chamber 110 and a second chamber 160 used to recover the target matters 126.

Referring to FIG. 5, an opening 112 may be formed at a lower portion of the density gradient material layer 130 in the first chamber 110. Although the first chamber 110 and the second chamber 160 are integrated with each other in FIG. 5, the first chamber 110 may also be independently used. In this case, density gradient materials of the density gradient material layer 130 may be partially discharged from the first chamber 110 as well as the complexes 145 through the opening 112 of the first chamber 110. The complexes 145 may be recovered by discharging the complexes 145 out of the first chamber 110. Although not shown, a valve may be installed at the opening 112 to control the discharging.

Figure 6:
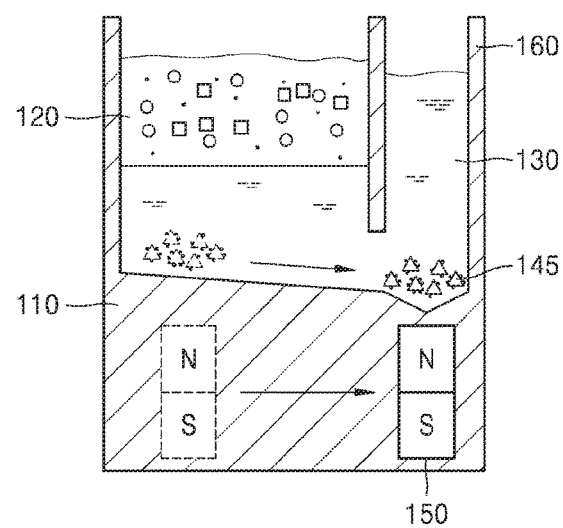
FIG. 6 is a diagram illustrating a extraction of a target matter by using a first chamber and a second chamber.

Alternatively, the second chamber 160 may be disposed at a side of the first chamber 110 in communication with the first chamber 110 through the opening 112 as illustrated in FIG. 5. FIG. 6 is a diagram illustrating an extraction of the target matters 126 by using the first chamber 110 and the second chamber 160.

Referring to FIG. 6, it may be confirmed that the complexes 145 may be recovered more stably using the second chamber 160. Although the second chamber 160 is isolated from the first chamber 110 by a barrier wall, the second chamber 160 may be in communication with the first chamber 110 through the opening 112 formed at a lower portion of the first chamber 110. Opening and closing of the opening 112 may be controlled by the valve as described above. The density gradient material of the density gradient material layer 130 contained in the first chamber 110 may be partially introduced into the second chamber 160 through the opening 112. The complexes 145 deposited at the bottom of the density gradient material layer 130 in the first chamber 110 may flow into the second chamber 160 through the opening 112 together with the density gradient material. In this regard, the bottom surface of the first chamber 110 may be slanted downwardly toward the second chamber 160 to facilitate the inflow of the complexes 145.

The magnetic field generating device 150 may be disposed in the first chamber 110. Particularly, the magnetic field generating device 150 may be disposed on the bottom surface of the first chamber 110. In addition, the magnetic field generating device 150 may draw the complexes 145 toward the second chamber 160 by changing a direction of the magnetic field while moving from the bottom surface of the first chamber 110 to the bottom surface of the second chamber 160. FIG. 6 exemplarily illustrates that the magnetic field generating device 150 moves inside the first chamber 110 and the second chamber 160, without being limited thereto. That is, the magnetic field generating device 150 may move in a state of being disposed outside the first chamber 110 and the second chamber 160.

Figure 7:
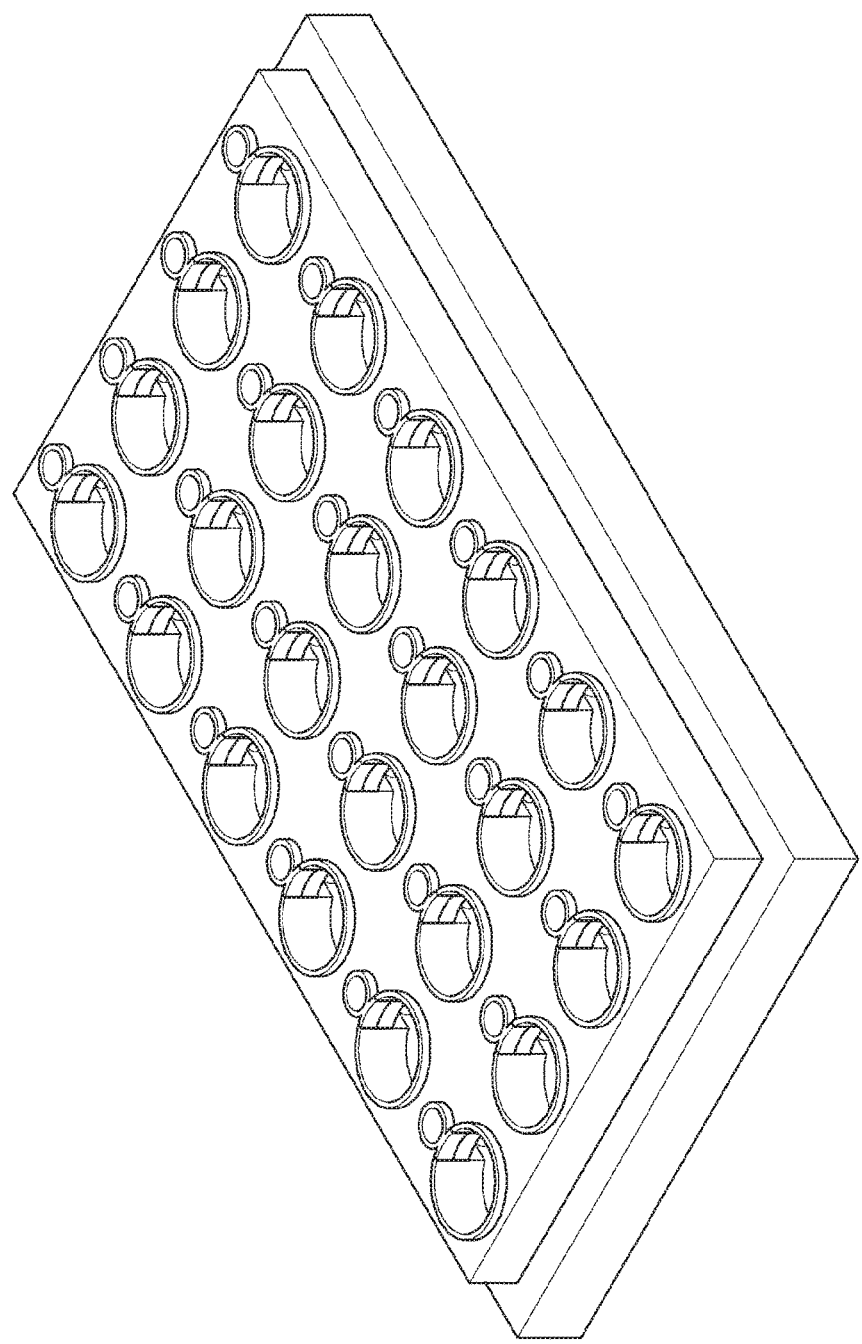
FIG. 7 is a perspective view of an array in which a plurality of sets each including the first chamber and the second chamber illustrated in FIGS. 5 and 6 are arrayed.

FIG. 7 is a perspective view of an array in which a plurality of sets each including the first chamber 110 and the second chamber 160 illustrated in FIGS. 5 and 6 are arrayed.

As illustrated in FIG. 7, a plurality of sets of the first chamber 110 and the second chamber 160 may constituted an array. The array may allow a plurality of samples to be tested simultaneously, thereby reducing time required for experiments. In addition, the magnetic field generating devices 150 may be respectively disposed at the bottom surfaces of the first chamber 110 and second chamber 160 in each set contained in the array.

Figure 8:
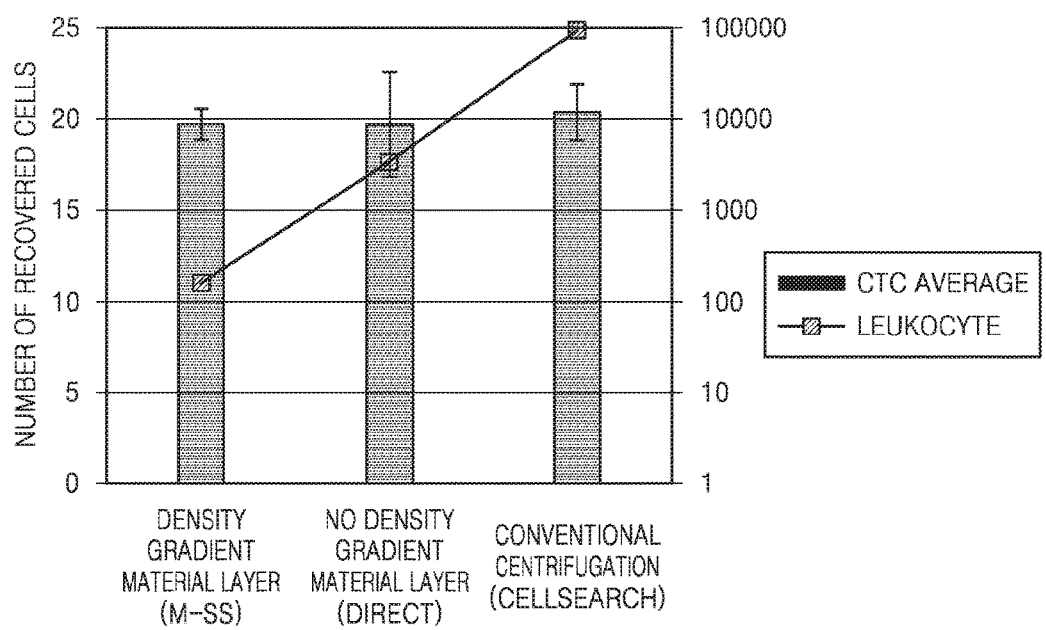
FIG. 8 is a graph illustrating experimental results obtained by using the target matter separating apparatus described with reference to FIGS. 1 to 7 and other apparatuses.

FIG. 8 is a graph illustrating experimental results obtained by using the target matter separating apparatus 100 described above with reference to FIGS. 1 to 7 and other apparatuses.

3 mL of blood were spiked with 100 cells of a cell line SHP-77 in the experiments illustrated in FIG. 8. A right bar 810 of FIG. 8 illustrates results regarding a ferrofluids product manufactured by CellSearch. A central bar 820 illustrates results obtained using the magnetic beads 140 and the magnetic field generating device 150 except for the density gradient material layer 130 in the target matter separating apparatus 100 illustrated in FIG. 1. A left bar 830 illustrates results obtained using the target matter separating apparatus 100 described above with reference to FIGS. 1 to 7. The bar graph of FIG. 8 indicates the numbers of recovered CTCs, and a line graph of FIG. 8 indicates the numbers of leukocytes contained in recovered resultants. The CTCs and leukocytes were identified using DAPI, CK-PE, and SD45-APC reagents. CTCs exhibit fluorescence in the DAPI and CK-PE reagents and do not exhibit fluorescence in the SD45-APC reagent. On the other hand, leukocytes exhibit fluorescence in the DAPI and CD45-APC reagents, but do not exhibit fluorescence in the CK-PE reagent. Thus, leukocytes and CTCs may be distinguished from each other by only using fluorescence in these reagents.

Referring to FIG. 8, although the extraction rates of SHP-77 are similar in the three cases, the amounts of the leukocytes mixed in the resultants are different. It may be confirmed that the amount of leukocytes is about 10 to about 100 times less than that of the ferrofluids product manufactured by CellSearch even when the density gradient material layer 130 is not used. In addition, the amount of leukocytes when the density gradient material layer 130 is used is at least 10 times less than that of the leukocytes when the density gradient material layer 130 is not used. In conclusion, the purity of the target matters obtained by the target matter separating apparatus 100 according to an exemplary embodiment is about 100 to about 1000 times greater than that obtained using the product of CellSearch. Particularly, a log depletion value, which indicates a contamination amount of the target matters by leukocytes when a washing process was not performed, in the case of using the product of CellSearch was 2.03. However, a log depletion value obtained using the target matter separating apparatus 100 was 4.79. That is, the difference in the amounts of the leukocytes is about 575 times.

Figure 9:
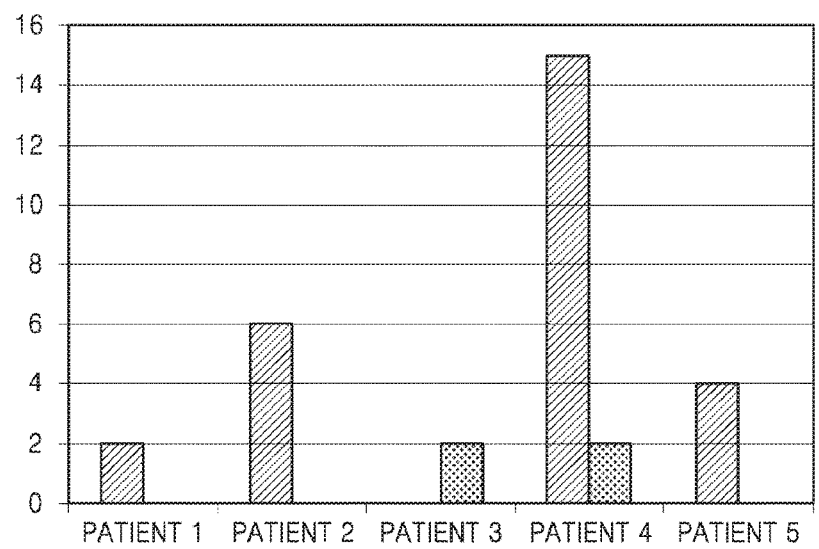
FIG. 9 is a graph illustrating experimental results of CTCs contained in actual blood, obtained by using the target matter separating apparatus described above with reference to FIGS. 1 to 7 and other apparatuses.

FIG. 9 is a graph illustrating experimental results of CTCs contained in actual blood, which are obtained using the target matter separating apparatus 100 described above with reference to FIGS. 1 to 7 and other apparatuses.

FIG. 9 illustrates experimental results of five actual patients. 5 mL of blood of each of five advanced breast cancer patients were used. A vertical axis of the graph of FIG. 9 indicates extraction rates of CTCs. Dashed line bars with in FIG. 9 indicate the results obtained using the target matter separating apparatus 100 according to an exemplary embodiment. In addition, dot bars (.) indicate the results obtained using the product of Cellsearch. Referring to FIG. 9, it may be confirmed that extraction rates of CTCs obtained using the target matter separating apparatus 100 according to an exemplary embodiment are higher than those obtained using the product of the Cellsearch in the blood of 4 patients out of 5 patients. Particularly, in Patents 1, 2, and 5, CTCs were identified using the target matter separating apparatus 100 although the product of CellSearch could not detect the existence of the CTCs.

The target matter separating apparatus 100 according to an exemplary embodiment is described above. Hereinafter, a method of separating the target matter by using the target matter separating apparatus 100 will be described. Descriptions presented above with reference to the target matter separating apparatus 100 may also be applied to the method of separating the target matter.

Figure 10:
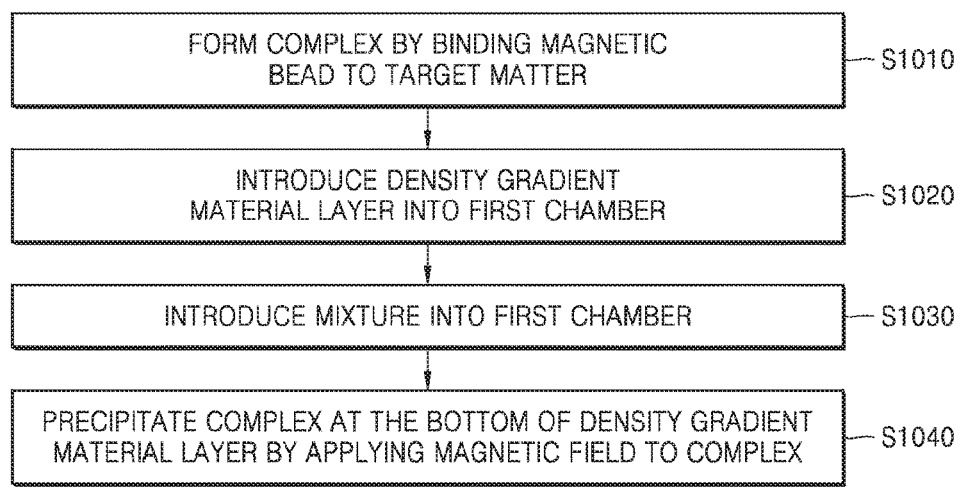
FIG. 10 is a flowchart of a method of separating a target matter according to an exemplary embodiment.

FIG. 10 is a flowchart illustrating a method 1000 of separating a target matter according to an exemplary embodiment. Referring to FIG. 10, the target matter separating method 1000 includes forming complexes 145 by binding magnetic beads 140 including magnetic materials to target matters 126 (S1010), introducing a density gradient material layer 130 having a greater density than a density of a mixture 120 into a first chamber 110 (S1020), introducing the mixture 120 into the first chamber 110 (S1030), and precipitating the complexes 145 at the bottom of the density gradient material layer 130 by applying a magnetic field to the complexes 145 (S1040). However, the order of operations are not limited by the reference numerals of the operations. For example, the magnetic beads 140 may bind to the target matters 126 before the mixture 120 is introduced into the first chamber 110. Alternatively, the magnetic beads 140 may bind to the target matters 126 after the mixture 120 is introduced into the first chamber 110.

Since the density of the mixture 120 is smaller than that of the density gradient material layer 130 as described above, the mixture 120 may be maintained on the density gradient material layer 130. Types of the mixture 120 may vary. For example, blood may be used as the mixture 120, and CTCs may be used as the target matters 126. In addition, the magnetic beads 140 may have various densities greater than that of the density gradient material layer 130. In addition, the magnetic beads 140 may include ligands capable of specifically binding to surface markers contained in the target matters 126 as described above. The surface marker may include at least one selected from the group consisting of EpCAM, c-Met, cytokeratines, CD45, Her2, Caveolin, EGFR, and IGFR existing on the surfaces of the CTCs, and the ligand may include an antibody binding to the EpCAM surface marker.

The target matter separating method 1000 may further include moving the complexes 145 precipitated at the bottom of the density gradient material layer 130 into the second chamber 160 in communication with the first chamber 110 by applying a magnetic field to the complexes 145.

Hereinafter, the target matter separating apparatus 100 and the target matter separating method 1000 according to an exemplary embodiment are described above with reference to FIGS. 1 to 10. According to the target matter separating apparatus 100 and the target matter separating method 1000, the target matters 126 may be efficiently separated with high extraction rate and high purity.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for separating a target matter, comprising:
a mixture comprising a target matter;
a density gradient material layer disposed under the mixture and having a greater density than a density of the mixture;
magnetic beads comprising a magnetic material and binding to the target matter to form a complex;
a magnetic field generating device configured to apply a magnetic field to the complex to precipitate the complex at the bottom of the density gradient material layer;
a first chamber configured to accommodate the mixture and the density gradient material layer, wherein an opening is formed at a lower portion of the density gradient material layer, and wherein the complex is precipitated at the bottom of the first chamber; and
a second chamber in communication with the first chamber through the opening, wherein the magnetic field generating device is further configured to move the complex from the first chamber to the second chamber by applying a magnetic field to the complex to draw the complex toward the second chamber,
wherein the complex moved to the second chamber is extracted from the second chamber.

2. The apparatus for separating a target matter of claim 1, wherein the mixture comprises at least one selected from the group consisting of blood, bone marrow, saliva, tear, urine, semen, or mucous fluid.

3. The apparatus for separating a target matter of claim 1, wherein the target matter comprises circulating tumor cells (CTCs).

4. The apparatus for separating a target matter of claim 2, wherein the mixture is blood, and a density of the density gradient material layer is greater than a density of a leukocyte contained in the blood.

5. The apparatus for separating a target matter of claim 1, wherein a density of the magnetic bead is greater than a density of the density gradient material layer.

6. The apparatus for separating a target matter of claim 1, wherein a density of the density gradient material layer is in a range of about 1.077 g/mL to about 1.2 g/mL.

7. The apparatus for separating a target matter of claim 1, wherein the magnetic bead comprises a paramagnetic bead.

8. The apparatus for separating a target matter of claim 1, wherein the magnetic bead comprises a ligand specifically binding to a surface marker contained in the target matter.

9. The apparatus for separating a target matter of claim 8, wherein the target matter comprises CTCs, the surface marker comprises at least one selected from the group consisting of EpCAM, c-Met, cytokeratines, CD45, Her2, Caveolin, EGFR, and IGFR existing on the surfaces of the CTCs, and the ligand comprises an antibody capable of binding to the surface marker.

10. The apparatus for separating a target matter of claim 1, wherein a lower surface of the first chamber is downwardly slanted toward the second chamber.

11. A method of selectively separating a target matter contained in a mixture, the method comprising:
forming a complex by binding magnetic beads comprising a magnetic material to the target matter;
introducing a density gradient material layer having a greater density than a density of the mixture into a first chamber;
introducing the mixture into the first chamber;
precipitating the complex at the bottom of the first chamber by applying a magnetic field to the complex using a magnetic field generating device;
moving the complex from the first chamber to a second chamber by applying a magnetic field to the complex using the magnetic field generating device; and
extracting the complex moved to the second chamber from the second chamber,
wherein the first chamber is configured to accommodate the mixture and the density gradient material layer, wherein an opening is formed at a lower portion of the density gradient material layer, and wherein the second chamber is in communication with the first chamber through the opening.

12. The method of claim 11, wherein a density of the magnetic bead is greater than a density of the density gradient material layer.

13. The method of claim 11, wherein the magnetic bead comprises a ligand capable of specifically binding to a surface marker contained in the target matter.

14. The method of claim 11, wherein the target matter comprises CTCs, the surface marker comprises at least one selected from the group consisting of EpCAM, c-Met, cytokeratines, CD45, Her2, Caveolin, EGFR, and IGFR existing on the surface of the CTCs, and the ligand comprises an antibody capable of binding to the surface marker.

* * * * *